United States Patent [19]
Davis et al.

[11] Patent Number: 4,675,445

[45] Date of Patent: Jun. 23, 1987

[54] PROCESS FOR ELIMINATION N-NITROSAMINES FROM N-NITROSAMINE-CONTAINING COMPOSITIONS

[75] Inventors: Pauls Davis, Gibraltar; Donald C. Mente, Grosse Ile, both of Mich.

[73] Assignee: BASF Corporation, Wyandotte, Mich.

[21] Appl. No.: 796,850

[22] Filed: Nov. 12, 1985

Related U.S. Application Data

[63] Continuation-in-part of Ser. No. 671,680, Nov. 15, 1984, abandoned.

[51] Int. Cl.$^4$ .............................................. C07C 85/26
[52] U.S. Cl. ................................... 564/437; 564/112; 564/411; 564/413; 564/416; 564/441; 564/463; 564/494; 564/497

[58] Field of Search ............... 564/112, 411, 413, 416, 564/437, 441, 463, 494, 497

[56] References Cited

U.S. PATENT DOCUMENTS 4,537,992  8/1985  Pikarski et al. ..................... 564/437

*Primary Examiner*—Charles F. Warren
*Assistant Examiner*—John A. Sopp
*Attorney, Agent, or Firm*—William G. Conger

[57] ABSTRACT

A process for eliminating N-nitrosamines, particularly N,N-dialkyl-N-nitrosamines and N-alkyl-N-aryl-N-nitrosamines from N-nitrosamine containing compositions through the addition of organic carboxylic acid halides. The process eliminates N-nitroso compounds without rearrangement to C-nitroso compounds.

25 Claims, No Drawings

PROCESS FOR ELIMINATION N-NITROSAMINES FROM N-NITROSAMINE-CONTAINING COMPOSITIONS

This is a continuation-in-part of applicants' copending application, Ser. No. 671,680 filed Nov. 15, 1984, now abandoned.

BACKGROUND OF THE INVENTION

1. Field of the Invention

The subject invention relates to a process for eliminating N-nitrosamines from N-nitrosamine-containing compositions. More specifically, the subject invention relates to the removal of N-nitrosamine impurities which are typically found in intermediates and finished products in the dye, pigment, pharmaceutical and herbicide industries.

2. Description of the Prior Art

N-nitrosamines are found in a wide variety of products in amounts ranging from trace amounts barely detectable by the most modern equipment to fairly large quantities, approaching 30 percent by weight in some instances. Natural products such as Scotch whiskey and beer have also been shown to contain small quantities of these substances.

The formation of N-nitrosamines in the many products in which they occur apparently takes place by a variety of mechanisms, at least some of which are still unknown. In the manufacture of many dyes and pesticides, however, it is believed that trace amounts of nitrosating agents derived from prior nitration processes in nitro-substituted intermediates react subsequently with amines or substituted amines to form the corresponding N-substituted-N-nitrosamines. For example, in the manufacture of trifluralin herbicide, N,N-dipropylamine is reacted with 1-chloro-2,6-dinitro-4-(trifluoromethyl)benzene. During the process N-nitroso-N,N-dipropylamine is formed as an impurity in amounts up to several hundred parts per million (ppm).

Many N-nitrosamines are highly toxic. N,N-dimethylnitrosamine, for example, has a $LD_{50}$ of only 10 mg/Kg. Of greater significance than their toxicity, however, are potential carcinogenic, mutagenic, and teratogenic effects. Many, if not most N-nitrosamines, are classified as animal carcinogens by OSHA, for example.

Because of the aforementioned deleterious health-related effects, stringent limitations have been placed upon the permissible amounts of N-nitrosamine impurities in consumer products such as cosmetics, pharmaceuticals, pesticides, dyes and pigments. Because of the exceptionally low allowable limits for N-nitrosamine impurities in these products, their virtually complete removal or destruction has often been problematic.

One conceivable method of eliminating N-nitrosamines from products is to prevent their formation in the first place. Elimination of nitrosating agents as a means of decreasing N-nitrosamine formation is disclosed in U.S. Pat. No. 4,120,905, for example, where a 1-chloro-2,6-dinitro-4-(trifluoromethyl)benzene intermediate is stripped of nitrosating agents with the aid of a non-reactive gas at a temperature of 50° C. to 100° C. in an aqueous alkaline solution. Unfortunately, a two-step treatment with large quantities of solution are required to achieve levels of less than ca. 10 ppm of N-nitrosamine following reacting of the "nitrosating agent free" intermediate with N,N-dipropylamine. This residual N-nitrosamine concentration is still too high for commercial products. Furthermore, the disposal of large quantities of aqueous alkali is necessitated by this process.

Perhaps the oldest and most effective method of N-nitrosamine destruction involves heating with concentrated hydrochloric acid. This process, for example, was well described by Renouf in Berichte 13, pp. 2169–74 (1880), and, in conjunction with the use of anhydrous hydrogen chloride, is the subject of U.S. Pat. No. 4,226,789. According to the process of U.S. Pat. No. 4,226,789, N-nitrosamines may be removed from dinitroaniline herbicides by heating with concentrated hydrochloric acid. Generally, 10 percent to 30 weight percent of concentrated hydrochloric acid relative to the weight of N-nitrosamine-containing product is used where the amount of N-nitrosamine impurity is relatively small (<1000 ppm). The mixture is agitated for a time period of from 0.25 hour to several hours at a temperature above the melting point of the product, generally from 70° C. to 90° C. The residual N-nitrosamine level is generally less than 1 ppm utilizing this method.

Unfortunately, the large quantities of concentrated hydrochloric acid utilized in the process of U.S. Pat. No. 4,226,789 and the attendant problems of equipment corrosion, neutralization and washing of the product, and disposal of large quantities of acid waste render this process less than ideal.

The process of U.S. Pat. No. 4,185,035 is similar to that of U.S. Pat. No. 4,226,789 except that inorganic halides such as $PCl_3$, $PBr_3$, $POCl_3$, $TiCl_4$, and $SO_2Cl_2$, are utilized in place of hydrochloric acid. The inorganic halides used in this process, however, are difficult to handle, volatile, corrosive, and toxic. Moreover, some of the inorganic halides, especially those containing sulfur or heavy metals give rise to toxic by-products which, in turn, can cause a waste disposal problem. Furthermore, the use of these inorganic halides does not appear to reduce the N-nitrosamine levels to those obtainable with concentrated hydrochloric acid.

U.S. Pat. No. 4,134,917 describes a process for the denitrosation of organic N-nitrosamines by the addition of an aldehyde or ketone In the presence of strong acid. This process is capable of eliminating large quantities of N-nitrosamines, but requires considerable quantities of concentrated hydrochloric acid as does the process of U.S. Pat. No. 4,426,789. Furthermore, the N-nitrosamine impurity levels, while considerably lower than their initial values, are much too high for applications such as food dyes, cosmetics, and herbicides. Residual levels of N-nitrosamines of 0.01 percent, or 100 ppm, are typical, for example, with the best results reported to be ca. 10 ppm.

SUMMARY OF THE INVENTION

None of the prior art processes is entirely satisfactory for the destruction or removal of N-nitrosamines from commercial products. Desirable features of an N-nitrosamine elimination process incude the use of an N-nitrosamine eliminating or decomposing agent which is inexpensive and readily available, which can be used in small quantities relative to the quantity of the commercial product. The end products of this reaction must possess neither the toxicity of the nitrosamine impurity nor cause appreciable environmental impact with regard to waste disposal.

It is therefore an object of the subject invention to provide a process for the elimination of N-nitrosamines from N-nitrosamine-containing compositions. It is a further object of the invention to utilize as N-nitrosamine eliminating agents, chemical substances which are readily commercially available or easily synthesized. A still further object of the invention is to provide a process for the elimination of N-nitrosamines from commercial products, the waste by-products of which place little or no stress upon the environment.

These objectives were surprisingly met by the addition, to the N-nitrosamine-containing product, of an N-nitrosamine eliminating amount of one or more organic acyl halides having the formula:

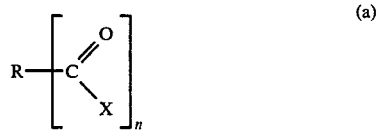

(a)

wherein R is a radical of valence n, derived from an aliphatic, cycloaliphatic aromatic or arylaliphatic hydrocarbon containing from 1 to about 20 carbon atoms, n is an integer from 1 to 3, and x is chlorine, bromine, or iodine. The addition of relatively small amounts, i.e., 2 percent by weight based upon the total weight of N-nitrosamine-containing product is effective in eliminating N-nitrosamines after a short incubation period at moderate temperatures from compositions not containing excessive amounts of N-nitrosamines.

DESCRIPTION OF THE PREFERRED EMBODIMENTS

A large number of acyl halide are suitable for eliminating N-nitrosamines by the process of the subject invention. Those most suitable are those acyl halides which are commercially available, inexpensive, and which produce no objectionable reacion products. Of the commercially available acyl halides, the chlorides are generally the least expensive and have the advantage that the by-product chloride ion, when released in small quantities, places little stress on the environment. Acyl chlorides are thus preferred as N-nitrosamine eliminating agents. Acyl bromides and acyl iodides are generally more reactive than acyl chlorides but are considerably more expensive, toxic, commercially less available, and have a greater environmental impact. The iodides in particular, while having excellent reactivity, are quite toxic. Therefore their use should be avoided except for exceptional circumstances. While the acyl bromides may be conveniently utilized, the use of acyl chlorides is preferred.

Suitable acyl chlorides include the substituted and unsubstituted carboxylic acid chlorides, for example, ethanoic acid chloride (acetyl chloride), propanoic acid chloride, butanoic acid chloride, cyclohexanoic acid chloride, benzoic acid chloride, 2-chloroethanoic acid chloride, 2,2,-dichloroethanoic acid chloride, 2,2,2-trichloro- and 2,2,2-trifluoroethanoic acid chloride, benzylic acid chloride, 2-phenyl-1-propanoic acid chloride, 2-ethylhexanoic acid chloride, 1,6-hexanedioic acid chloride. The corresponding acyl bromides and iodides may also be utilized. Preferably used are monocarboxylic acid chlorides such as ethanoic acid chloride and propanoic acid chloride. While the halogen substituted acid chlorides may be effective, their use leaves halogen substituted reaction products in the final composition. As it is well known that these products are deleterious to the environment, the use of such acid chlorides, such as 2,2,2-trichloroacetyl chloride, is generally not recommended. Because of its ready availability, low price, and the low toxicity of its by-products, the use of ethanoic acid chloride is especially preferred.

The amount of N-nitrosamine eliminating agent is not critical, but in order for residual levels of N-nitrosamines to be less than 1 ppm, at least one mole equivalent of acyl halide per mole of N-nitrosamine must be utilized. Generally, it is convenient to calculate the amount of N-nitrosamine eliminating acyl halide to be added on the basis of the weight of product rather than the weight of N-nitrosamine present, especially when the N-nitrosamine level is low to begin with, for example, less than ca. 1000 ppm. This procedure avoids the necessity of performing a time-consuming N-nitrosamine analysis prior to N-nitrosamine destruction. In this case, only an analysis of the N-nitrosamine content of the final product is necessary.

Generally, less than 10 percent by weight of acyl halide based upon overall product weight need be added. With low levels of N-nitrosamines, considerably smaller quantities are required, for example, ca. 2 percent or less. Of course with dyes and pigments or other compositions containing much higher N-nitrosamine levels, correspondingly larger amounts of N-nitrosamine eliminating acyl halide must be added. Because N-nitrosamine eliminating agents such as ethanoic acid chloride are inexpensive, addition of a large excess over the amount of N-nitrosamine to be eliminated is economically feasible and promotes rapid reaction as well as virtually complete N-nitrosamine elimination. Elimination of N-nitrosamines to below the level detectible by Thermal Energy Analysis (TEA) of 0,3 ppm is routinely achieved.

The acyl halide may be added gradually to the N-nitrosamine-containing product, or it may be added all at once. The product should be liquid, i.e., above its melting point, or dissolved in a suitable non-aqueous and preferably aprotic solvent. The reaction mixture should be essentially free from water, although relatively small amounts of water can be tolerated. Under these conditions, however, a larger quantity of acyl halide may be necessary for the desired degree of N-nitrosamine elimination. Reaction conditions which are substantially anhydrous are preferred, especially when elimination of N-aryl-N-nitrosamines is desired, due to the possibility of various rearrangements which may occur in certain circumstances.

The elimination of N-nitrosamines proceeds at room temperature, or even below, but higher temperatures are generally preferred. Temperatures from 40° C. to 70° C. are especially preferred. Temperatures higher than 70° C. are usually not required and are undesirable due to increased volatization of the acyl halide. With suitable process equipment and acyl halides, however, or due to an unusually high melting product requiring their use, high temperatures may be utilized when necessary.

The N-nitrosamines which may be eliminated by the process of the present invention include secondary N-nitrosamines corresponding to the formula

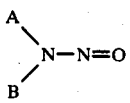

where A and B may individually be alkyl and aryl, the alkyl designation including, in addition to normal, secondary, and tertiary alkyl groups, cycloalkyl, and aralkyl groups. The N-nitrosamines which cause the greatest concern are the N,N-disubstituted-N-nitrosamines, where the substituents are alkyl or cycloalkyl groups. Examples are N,N-dimethyl-N-nitrosamine, N,N-diethyl-N-nitrosamine, N,N-di(n-propyl)-N-nitrosamine, N,N-di(2-propyl)-N-nitrosamine, N-(n-propyl)-N-(2-propyl)-N-nitrosamine, N-methyl-N-cyclopropyl-N-nitrosamine, N-ethyl-N-cyclopropyl-N-nitrosamine, N-propyl-N-cyclopropyl-N-nitrosamine, N,N-dicyclopropyl-N-nitrosamine, N-methyl-N-(n-butyl)-N-nitrosamine, N-ethyl-N-(n-butyl)-N-nitrosamine, N-(n-propyl)-N-(n-butyl)-N-nitrosamine, N-cyclopropyl-N-(n-butyl)-N-nitrosamine, N-methyl-N-cyclopropylmethyl-N-nitrosamine, N-ethyl-N-cyclopropylmethyl-N-nitrosamine, N-propyl-N-cyclopropylmethyl-N-nitrosamine, N-methyl-N-(2-butyl)-N-nitrosamine, N-ethyl-N-(2-butyl)-N-nitrosamine, N,N-di(2-butyl)-N-nitrosamine, and N,N-dioctyl-N-nitrosamine. This list of alkyl and cycloalkyl-N-nitrosoamines which the process of the subject invention can be used to eliminate is by way of example and is far from exhaustive.

The process of the subject invention may also be used to eliminate N-nitrosamines when either A, B, or both in the foregoing formula are derived from aryl groups. When such aryl groups are present, however, care must be exercised that the particular N-aryl-N-substituted-N-nitrosamine does not rearrange to form potentially carcinogenic and therefore equally undesirable aryl-C-nitrosamines.

Such rearrangement is possible when an aryl ring, which is not substituted by deactivating groups, is unsubstituted at the para-, or 4-position from the amino group and the elimination reaction takes place in an aqueous or protic environment. The rearrangement of aryl-N-nitrosamines to amino aryl-C-nitroso compounds is known as the Fischer-Hepp rearrangement. This rearrangement, as previously mentioned, takes place in a protic solvent, usually water or alkanol, in the presence of hydrochloric acid or hydrogen chloride. For example the nitrosoanilines may be rearranged as follows:

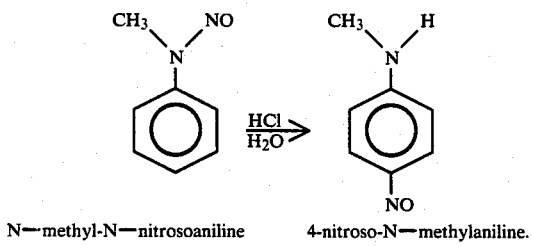

N—methyl-N—nitrosoaniline    4-nitroso-N—methylaniline.

The rearrangement fails when the 4-position is blocked and when the aromatic ring is deactivated.

To avoid the possibility of rearrangement to C-nitroso compounds when eliminating N-aryl-N-substituted-N-nitrosamines, it is advisable to operate in a substantially anhydrous and aprotic solvent and to avoid those N-aryl systems which are unsubstituted at the 4-position and are not deactivated. Examples of N-aryl-N-substituted-N-nitrosamines which may be eliminated by the process of the subject invention without any possibility of C-nitroso compound formation even in the presence of minor amounts of water or protic solvents are the various N-aryl-p-substituted-N-nitroso-anilines corresponding to the formula:

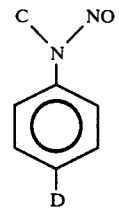

where C is alkyl or cycloalkyl and D is a substituent other than hydrogen. Examples of these are: N-methyl-4-methyl-N-nitrosoaniline, N-methyl-4-methoxy-N-nitrosoaniline, N-methyl-4-chloro-N-nitrosoaniline, N-methyl-4-phenyl-N-nitrosoaniline, N-methyl-4-(N-nitrosamino)benzoic acid, N-methyl-4-nitro-N-nitrosoaniline, N-methyl-N-nitrosoaniline-4-sulfonic acid, N-methyl-4-trifluoromethyl-N-nitrosoaniline, N-ethyl-4-methyl-N-nitrosoaniline, N-ethyl-4-methoxy-N-nitrosoaniline, N-ethyl-4-chloro-N-nitrosoaniline, N-ethyl-4-phenyl-N-nitrosoaniline, N-ethyl-4-(N-nitrosamino)benzoic acid, N-ethyl-4-nitro-N-nitrosoaniline, N-ethyl-N-nitrosoaniline-4-sulfonic acid, N-ethyl-4-trifluoromethyl-N-nitrosoaniline, N-propyl-4-methyl-N-nitrosoaniline, N-propyl-4-methoxy-N-nitrosoaniline, N-propyl-4-chloro-N-nitrosoaniline, N-propyl-4-phenyl-N-nitrosoaniline, N-propyl-4-(N-nitrosamino)benzoic acid, N-propyl-4-nitro-N-nitrosoaniline, N-propyl-N-nitrosoaniline-4-sulfonic acid, N-propyl-4-trifluoromethyl-N-nitrosoaniline, N-(n-butyl)-4-methyl-N-nitrosoaniline, N-(n-butyl)-4-methoxy-N-nitrosoaniline, N-(n-butyl)-4-chloro-N-nitrosoaniline, N-(n-butyl)-4-phenyl-N-nitrosoaniline, N-(n-butyl)-4-(N-nitrosamino)benzoic acid, N-(n-butyl)-4-nitro-N-nitrosoaniline, N-(n-butyl)-N-nitrosoaniline-4-sulfonic acid, N-(n-butyl)-4-trifluoromethyl-N-nitrosoaniline, N-(2-butyl)-4-methyl-N-nitrosoaniline, N-(2-butyl)-4-methoxy-N-nitrosoaniline, N-(2-butyl)-4-chloro-N-nitrosoaniline, N-(2-butyl)-4-phenyl-N-nitrosoaniline, N-(2-butyl)-4-(N-nitrosamino)benzoic acid, N-(2-butyl)-4-nitro-N-nitrosoaniline, N-(2-butyl)-N-nitrosoaniline-4-sulfonic acid, N-(2-butyl)-4-trifluoromethyl-N-nitrosoaniline, N-(n-pentyl)-4-methyl-N-nitrosoaniline, N-(n-pentyl)-4-methoxy-N-nitrosoaniline, N-(n-pentyl)-4-chloro-N-nitrosoaniline, N-(n-pentyl)-4-phenyl-N-nitrosoaniline, N-(n-pentyl)-4-(N-nitrosamino)benzoic acid, N-(n-pentyl)-4-nitro-N-nitrosoaniline, N-(n-pentyl)-N-nitrosoaniline-4-sulfonic acid, N-(n-pentyl)-4-trifluoromethyl-N-nitrosoaniline, N-(2-pentyl)-4-methyl-N-nitrosoaniline, N-(2-pentyl)-4-methoxy-N-nitrosoaniline, N-(2-pentyl)-4-chloro-N-nitrosoaniline, N-(2-pentyl)-4-phenyl-N-nitrosoaniline, N-(2-pentyl)-4-(N-nitrosamino)benzoic acid, N-(2-pentyl)-4-nitro-N-nitrosoaniline, N-(2-pentyl)-N-nitrosoaniline-4-sulfonic acid, N-(2-pentyl)-4-trifluoromethyl-N-nitrosoaniline, N-(3-pentyl)-4-methyl-N-nitrosoaniline, N-(3-pentyl)-4-methoxy-N-nitrosoaniline, N-(3-pentyl)-4-chloro-N-nitrosoaniline, N-(3-pentyl)-4-phenyl-N-nitrosoaniline, N-(3-pentyl)-4-(N-nitrosamino)benzoic acid, N-(3-pentyl)-4-nitro-N-nitrosoaniline, N-(3-pentyl)-N- nitrosoaniline-4-sulfonic acid, N-(3-pentyl)-4-trifluoromethyl-N-nitrosoaniline, N-cyclopropyl-4-methyl-N-nitrosoaniline, N-cyclopropyl-4-methoxy-N-nitrosoaniline, N-cyclopropyl-4-chloro-N-nitrosoaniline, N-cyclopropyl-4-phenyl-N-nitrosoaniline, N-cyclopropyl-4-(N-nitrosamino)benzoic acid, N-cyclopropyl-4-nitro-N-nitrosoaniline, N-cyclopropyl-N-nitrosoaniline-4-sulfonic acid, N-cyclopropyl-4-trifluoromethyl-N-nitrosoaniline, N-cyclohexyl-4-methyl-N-nitrosoaniline, N-cyclohexyl-4-methoxy-N-nitrosoaniline, N-cyclohexyl-4-chloro-N-nitrosoaniline, N-cyclohexyl-4-phenyl-N-nitrosoaniline, N-cyclohexyl-4-(N-nitrosamino)benzoic acid, N-cyclohexyl-4-nitro-N-nitrosoaniline, N-cyclohexyl-N-nitrosoaniline-4-sulfonic acid, N-cyclohexyl-4-trifluoromethyl-N-nitrosoaniline, N-(cyclopropylmethyl)-4-methyl-N-nitrosoaniline, N-(cyclopropylmethyl)-4-methoxy-N-nitrosoaniline, N-(cyclopropylmethyl)-4-chloro-N-nitrosoaniline, N-(cyclopropylmethyl)-4-phenyl-N-nitrosoaniline, N-(cyclopropylmethyl)-4-(N-nitrosamino)benzoic acid, N-(cyclopropylmethyl)-4-nitro-N-nitrosoaniline, N-(cyclopropylmethyl)-N-nitrosoaniline-4-sulfonic acid, N-(cyclopropylmethyl)-4-trifluoromethyl-N-nitrosoaniline. Other N-alkyl or cycloalkyl-p-substituted N-nitrosoanilines may also be successfully eliminated by the process of the subject invention.

Ring-deactivated aromatic N-nitrosamines may also be eliminated by the process of the subject invention without the possibility of C-nitroso rearrangement. Such compounds are generally deactivated by the presence of one or more nitro groups. Preferably, these compounds correspond to the formula

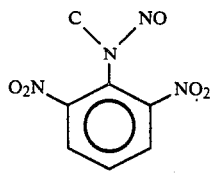

and even more preferably

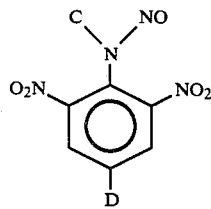

where C and D in both formulas are as previously defined.

Suitable examples of deactivated compounds are the N-alkyl-2-nitro-4-substituted-N-nitrosoanilines, for example where the alkyl group is a normal, secondary, tertiary, or cycloalkyl group and the 4-substituent is another normal, secondary, tertiary, or cycloalkyl group or halo-substituted derivatives thereof, or a chloro, bromo, methoxy, acetoxy, carboxy, sulfonyl, nitro or other group. Especially well suited are the N-alkyl-2,6-dinitro, 4-substituted-N-nitrosamines, for example N-methyl-2,6-dinitro-3,4-dimethyl-N-nitrosoaniline, N-(3-pentyl)-2,6-dinitro-3,4-dimethyl-N-nitrosoaniline and the various N-alkyl-2,6-dinitro-4-trifluromethyl-N-nitrosoanilines.

N,N-diaryl-N-nitrosamines may also be eliminated by the process of the subject invention provided the same aryl substitutions as previously described apply. Examples of N,N-diaryl-N-nitrosamines which may be successfully eliminated without fear of the formation of C-nitroso rearrangement products are, for example, N-nitroso-bis(4-methylphenyl)amine,

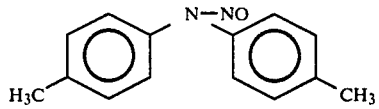

and various ring deactivated species.

Following N-nitrosamine destruction, residual unreacted acyl halide may be stripped from the product at reduced pressure, or with the aid of a nonreactive stripping gas such as air, or, for air-sensitive products, with the aid of carbon dioxide, nitrogen or other non-reactive gas. For low molecular weight products, the separation may also be achieved by conventional fractional distillation or wiped film evaporation. When small amounts of acyl halide are used, it may be possible to leave the unreacted residue in the product without attempting a separation.

For low molecular weight acyl halides it is possible to rapidly and effectively decompose any unreacted acyl halide by the addition of water to the product. Following the addition of water, the aqueous layer may be separated. Due to the small quantities of reaction products contained in the aqueous layer, disposal is generally not a problem and has little, if any, environmental impact. For acid-sensitive products, the product may then be washed with aqueous alkali or, alternatively, one washing with aqueous alkali may be used to remove the residual acyl halide instead of water alone or water followed by a dilute aqueous alkali wash.

A water wash will be ineffectual in removing the higher acid chlorides or their by-products, i.e., octanoic acid chloride and its hydrolysis product octanoic acid, due to the relatively low water solubility of these compounds. A water or aqueous alkaline wash may still be used in these cases, however, to remove any low molecular weight reaction products and, in the case of an alkaline wash, to neutralize the remaining carboxylic acid.

The examples which follow serve to illustrate the use of the subject invention, but do not serve to limit it in any way.

EXAMPLE 1

To a round bottom flask, containing 324.4 g trifluralin dissolved in an alkylated benzene solvent (TENNECO 500/100) at 30° C., was added 6.5 g ethanoic acid chloride. The crude trifluralin contained 6.3 ppm N-nitroso-N,N-dipropylamine as measured by TEA. The flask was stirred for one hour at a temperature of from 42° C. to 47° C., following which was added 15 g water. After separation from the aqueous layer, the trifluralin product solution contained no detectable N-nitrosamines (detection limit by TEA <0.3 ppm).

EXAMPLE 2

The procedure of Example 1 was followed, but excess, unreacted ethanoic acid chloride was removed by vacuum stripping at 70° C. The crude trifluralin contained 9.4 ppm N-nitroso-N,N-dipropylamine. Following addition of ethanoic acid chloride, but before stripping, the N-nitrosamine content was below the detectable limit. Following stripping, the N-nitrosamine content remained undetectable.

EXAMPLE 3

The procedure of Example 2 was followed. The crude trifluralin contained 10.0 ppm N-nitroso-N,N-dipropylamine. The product, both before and after stripping, contained no detectable N-nitrosamines.

For Examples 4–6, trifluralin was spiked with N-nitroso-N,N-diethylamine. To 1000 g trifluralin containing approximately 2 ppm N-nitroso-N,N-dipropylamine was added sufficient xylene to make a 68 percent by weight trifluralin solution. To this solution was added sufficient N-nitroso-N,N-diethylnitrosamine to raise the total N-nitrosamine concentration to 16.7 ppm by weight relative to the weight of solution.

EXAMPLE 4

To a round bottom flask was added 150 grams of the solution described above, containing 102 g trifluralin. Ethanoic acid chloride in an amount of 0.5 g (.5 percent by weight relative to trifluralin, 0.33 percent by weight relative to solution weight) was added and the mixture stirred for one hour at 70° C. The mixture was partially stripped at reduced pressure. Analysis indicated complete destruction of both the N-nitroso-N,N-dipropylamine as well as the N-nitroso-N,N-diethylamine.

EXAMPLE 5

Example 4 was repeated, except that 3.2 g propanoic acid chloride (3.1 percent by weight relative to trifluralin, 2.1 percent relative to total solution weight) was utilized in place of ethanoic acid chloride. Reaction time was 1.5 hours, and the mixture was not washed or stripped. Analysis indicated no detectable traces of either nitrosamine.

EXAMPLE 6

Example 5 was repeated, but 4.8 g octanoic acid chloride was used in place of propanoic acid chloride. The reaction was maintained at 70° C. for two hours. Analysis of the product mixture indicated complete elimination of both nitrosamines.

EXAMPLE 7

To a 10 g sample of N-methyl-2,6-dinitro-4-methylaniline dissolved in 100 g xylene, and containing 15 ppm of N-methyl-2,6-dinitro-4-methyl-N-nitrosoaniline is added 1 percent by weight of acetyl chloride. The mixture is stirred at 50° C. for one hour. No N-nitrosamines and no C-nitroso compounds are detectable.

The embodiments of the invention in which an exclusive privilege or property is claimed are defined as follows:

1. A process for the elimination of N-nitrosamines from N-nitrosamine-containing compositions comprising adding thereto an N-nitrosamine eliminating amount of one or more organic acyl halides having the formula:

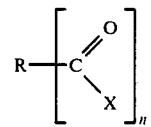

wherein R is a radical of valence n, derived from an aliphatic, cycloaliphatic, arylaliphatic, aromatic, or alkylaromatic hydrocarbon containing from 1 to about 20 carbon atoms, n is an integer from 1 to 3, and X is chlorine or bromine, and wherein said N-nitrosamine is selected from the gruop consisting of (a) N,N-dialkyl-N-nitrosamines, and (b) N-alkyl-N-aryl-N-nitrosamines and N,N-diarylnitrosamines which do not rearrange to form C-nitrosamines.

2. The process of claim 1 wherein R is —CH$_3$.
3. The process of claim 1 wherein R is —CH$_2$CH$_3$.
4. The process of claim 1 wherein R is CH$_3$(CH$_2$)$_6$—.
5. The process of claim 1 wherein R is —(CH$_2$)$_4$— and n is 2.
6. The process of claim 1 wherein X is Cl.
7. The process of claim 2 wherein X is Cl.
8. The process of claim 3 Wherein X is Cl.
9. The process of claim 4 wherein X is Cl.
10. The process of claim 5 wherein X is Cl.
11. A process for the elimination of N-nitrosamines from N-nitrosamine-containing dinitroaniline compositions comprising adding an N-nitrosamine eliminating amount of one or more organic acyl halides having the formula:

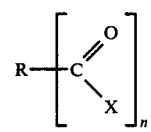

wherein R is a radical of valence n, derived from a aliphatic, cycloaliphatic, or arylaliphatic hydrocarbon containing from 1 to about 20 carbon atoms, n is an integer from 1 to 3, and x is chlorine or bromine, and wherein said N-nitrosamine is selected from the group consisting of (a) N,N-dialkyl-N-nitrosamines, and (b) N-alkyl-N-aryl-N-nitrosamines and N,N-diarylnitrosamines which do not rearrange to form C-nitrosamines.

12. The process of claim 11 wherein said dinitroaniline composition comprises a dinitroaniline herbicide composition wherein said herbicide is selected from the group consisting of benefin, isopropalin, ethalfluralin, fluchloralin, oryzalin, pendimethylin, profluralin, nitralin, and trifluralin.

13. The process of claim 12 wherein said N-nitrosamine containing composition is substantially anhydrous.

14. The process of claim 13 wherein said composition contains no solvent other than aprotic solvents.

15. The process of claim 11 wherein said N-nitrosamine is an N,N-dialkyl-N-nitrosamine wherein said alkyl group is selected from the group consisting of normal, secondary alkyl, tertiary alkyl and cycloalkyl groups.

16. The process of claim 11 wherein said N-nitrosamine is an N-alkyl-N-(nitroaryl)-N-nitrosamine substituted in the 4-aryl position by a member of the group consisting of alkyl of from 1 to 8 carbons, methoxy, trifluoromethyl, chloro, bromo, sulfonyl, carboxyl and nitro.

17. The process of claim 11 wherein said N-nitrosamine is N,N-dipropyl-N-nitrosamine.

18. The process of claim 11 wherein said N-nitrosamine is N-(3-pentyl)-3,4-dimethyl-2,6-dinitro-N-nitrosoaniline.

19. The process of claim 1 wherein said N-nitrosamine-containing composition is an organic dye or pigment.

20. The process of claim 1 wherein said N-nitrosamine-containing composition is a pharmaceutical composition.

21. The process of claim 1 wherein said N-nitrosamine-containing composition is a cosmetic composition.

22. The process of claim 1 wherein excess acyl halide is removed at reduced pressure.

23. The process of claim 1 wherein excess acyl halide is removed by vacuum stripping with the aid of a nonreactive gas.

24. The process of claim 1 wherein excess acyl halide is removed by means of washing with water.

25. The process of claim 1 wherein excess acyl halide is removed by washing with dilute aqueous alkali.

* * * * *